United States Patent [19]

Tanaka et al.

[11] Patent Number: 4,689,431
[45] Date of Patent: Aug. 25, 1987

[54] METHOD FOR THE PREPARATION OF PHENYL PYRUVIC ACID

[75] Inventors: Masato Tanaka, Yatabe; Kanji Ohtsuka, Tokyo, both of Japan

[73] Assignees: Japan as represented by General Director of Agency of Industrial Science and Technology; Nissan Chemical Industries, Ltd., both of Tokyo, Japan

[21] Appl. No.: 831,312

[22] Filed: Feb. 20, 1986

[30] Foreign Application Priority Data

Feb. 21, 1985 [JP] Japan ................................ 60-33193
Feb. 21, 1985 [JP] Japan ................................ 60-33194

[51] Int. Cl.$^4$ ............................................. C07C 51/10
[52] U.S. Cl. .................................................... 562/406
[58] Field of Search ........................................ 562/406

[56] References Cited

U.S. PATENT DOCUMENTS

| | | | |
|---|---|---|---|
| 3,116,306 | 12/1963 | Heck | 562/406 |
| 3,928,429 | 12/1975 | El-Chahawi | 562/406 |
| 4,128,578 | 12/1978 | Cassar | 562/406 |
| 4,152,352 | 5/1979 | Perron | 562/406 |
| 4,351,952 | 9/1982 | Foa | 562/406 |
| 4,447,644 | 5/1984 | El-Chahawi | 562/406 |
| 4,492,798 | 1/1985 | Lee | 562/406 |
| 4,576,809 | 3/1986 | Gauthier-Lafaye | 562/406 |

FOREIGN PATENT DOCUMENTS 60-61550 4/1985 Japan .

OTHER PUBLICATIONS

"Lange's Handbook of Chemistry," 12th Ed., pp. 10-60 to 10-62, (1979).

*Primary Examiner*—Michael L. Shippen
*Attorney, Agent, or Firm*—Hopgood, Calimafde, Kalil, Blaustein & Judlowe

[57] ABSTRACT

The invention provides an improvement in the method for the preparation of phenyl pyruvic acid by the reaction of benzyl chloride and carbon monoxide in a liquid reaction medium in the presence of a cobalt carbonyl as the catalyst. In the inventive method, the reaction is performed in the presence of calcium hydroxide and the reaction medium is a binary system composed of water and an organic solvent capable of dissolving the catalyst and not freely miscible with water. The reaction can proceed even under normal pressure and the desired product can be readily recovered in the form of precipitates of the calcium salt while the catalyst dissolved in the organic phase after completion of the reaction can be recycled and re-used as such in the next run so that the costs for the catalyst regeneration in the prior art can be entirely saved.

12 Claims, No Drawings

METHOD FOR THE PREPARATION OF PHENYL PYRUVIC ACID

BACKGROUND OF THE INVENTION

The present invention relates to a method for the preparation of phenyl pyruvic acid or, more particularly, to a method for the synthetic preparation of phenyl pyruvic acid by the reaction of benzyl chloride and carbon monoxide in the presence of a basic compound of an alkaline earth metal and a cobalt carbonyl compound as the catalyst.

As is known, phenyl pyruvic acid is an organic compound useful as a starting material for the synthesis of various kinds of compounds including phenyl alanine, which is a useful compound as an intermediate for the synthesis of, for example, an artificial sweetening agent, and others.

Among various synthetic routes for the preparation of phenyl pyruvic acid, the industrially most promising method is the reaction of benzyl chloride and carbon monoxide. It is proposed, for example, in Japanese Patent Publication No. 56-18587 corresponding to U.S. Pat. No. 4,152,352 that the reaction of benzyl chloride and carbon monoxide is catalyzed by a metal carbonyl compound or, preferably, a cobalt carbonyl as the catalyst and the reaction is performed in a binary solvent mixture of water and alcohol in the presence of a basic compound of an alkaline earth metal.

In the conventional methods for the preparation of phenyl pyruvic acid including the above mentioned proposal in the Japanese patent, the desired compound can readily be obtained by the treatment of the precipitates in the form of an alkali or alkaline earth metal salt of the acid, which is precipitated in the reaction mixture after completion of the reaction and recovered by filtration or other suitable means for solid-liquid separation, with an acid. A difficult problem, however, is encountered in these prior art methods in connection with the mutual separation and recovery of the phenyl acetic acid formed as a by-product in a considerable amount in the form of an alkali or alkaline earth metal salt and the cobalt carbonyl catalyst since both of the by-product and the catalyst are dissolved in the filtrate after recovery of the phenyl pyruvate. Moreover, the cobalt constituent, if separated from the filtrate solution, cannot be used as such for the catalytic purpose in the next run of the reaction without a very elaborate and troublesome procedure for the regeneration of the cobalt carbonyl catalyst.

To explain the regeneration procedure of the cobalt catalyst from the filtrate of the reaction mixture, the solvents, i.e. water and alcohol, are first removed from the solution by evaporation and the residue is treated with an inorganic acid to isolate the by-product phenyl acetic acid. The salt of cobalt with the inorganic acid is then converted into cobalt hydroxide by the treatment, for example, with an alkali hydroxide followed by the carbonylation reaction of the hydroxide with water gas into the cobalt carbonyl compound under a high pressure and at a high temperature. Thus, it is eagerly desired to reduce the costs for the cobalt catalyst.

Another problem in the above mentioned method as proposed in the Japanese patent is that the reaction must be performed under a pressurized condition of 5 to 200 bars or, preferably, at least 40 bars of the pressure in order to obtain an industrially practicable yield of the product. At least, the yield of the desired compound is quite low when the reaction is undertaken under normal pressure. Needless to say, a great advantage would be obtained if the reaction can be performed under normal pressure to give a satisfactorily high yield of the product.

SUMMARY OF THE INVENTION

An object of the present invention is therefore to provide a novel and improved method for the synthetic preparation of phenyl pyruvic acid in which the costs for the regeneration of the cobalt carbonyl catalyst can greatly be saved in the reaction of benzyl chloride and carbon monoxide catalyzed by a cobalt carbonyl compound along with easy recovery of the phenyl acetic acid produced as a by-product.

Another object of the invention is to provide a possibility of performing the reaction of benzyl chloride and carbon monoxide for the preparation of phenyl pyruvic acid under a pressure as low as possible or, desirably, under normal pressure so as to reduce the overall cost for the preparation of phenyl pyruvic acid.

Thus, the invention provides an improvement which comprises, in the method for the preparation of phenyl pyruvic acid by the reaction of benzyl chloride and carbon monoxide in the presence of a cobalt carbonyl compound as a catalyst and a basic compound of an alkaline earth metal, performing the reaction in a binary solvent system composed of water and an organic solvent, which is capable of dissolving the catalyst and not freely miscible with water at room temperature, as the reaction medium.

The above mentioned organic solvent is preferably a ketone solvent such as methyl isobutyl ketone and acetophenone. When these ketone solvents are used in combination with water in the reaction medium, the desired reaction can proceed with a sufficient velocity even under very mild conditions of, for example, normal pressure. Furthermore, the liquid phase after separation of the phenyl pyruvate by filtration is separated into two phases of aqueous and organic layers while the cobalt carbonyl catalyst is contained in the organic layer as dissolved therein, the phenyl acetic acid being dissolved in the aqueous phase in the form of a salt, and can be re-used as such in the next run of the reaction so that the expensive procedure of the catalyst regeneration in the prior art methods can be entirely omitted.

DETAILED DESCRIPTION OF THE PREFERRED EMBODIMENTS

As is understood from the above given summarizing description, the most characteristic feature of the inventive method consists in the use of a binary solvent system as the reaction medium which is composed of water and an organic solvent not freely miscible with water at room temperature. The organic solvents satisfying this definition are exemplified by aromatic hydrocarbons, e.g. benzene and toluene, aliphatic and aromatic ethers, e.g. diethyl ether, diisopropyl ether and diphenyl ether, and aliphatic and aromatic ketones, e.g. methyl isobutyl ketone, acetophenone, diisopropyl ketone, methyl isopropyl ketone, dibutyl ketone, diisobutyl ketone and cyclopentanone, of which the ketones are preferred with methyl isobutyl ketone and acetophenone as the most preferable species.

In preparing the reaction mixture, benzyl chloride as the starting reactant is used usually in an amount in the range from 1 to 50% by weight based on the amount of the above mentioned organic solvent, though not particularly limitative thereto. The binary solvent system is formed of the organic solvent and water, usually, in an amount in the range from 10 to 200% by weight based on the amount of the organic solvent.

The basic compound of an alkaline earth metal contained in the reaction mixture according to the invention is selected from the group consisting of hydroxides, oxides and carbonates of alkaline earth metals, of which hydroxides are preferred with calcium hydroxide as the most preferable species.

The amount of the basic compound of an alkaline earth metal in the reaction mixture should be at least equimolar to the benzyl chloride as the reactant. Preferably, the amount thereof should be in the range from 1.1 to 5.0 moles or, preferably, from 1.1 to 2.5 moles per mole of the benzyl chloride.

Exemplary of the catalyst to effectively promote the reaction in the inventive method are cobalt carbonyl compounds, of which dicobalt octacarbonyl is particularly preferred. The cobalt carbonyl catalyst should be added to the reaction mixture in an amount in the range from 0.01 to 1 mole or, preferably, from 0.05 to 0.33 mole per mole of the benzyl chloride.

The purity of carbon monoxide as the reactant to react with benzyl chloride is not particularly limitative and, if desired, water gas can be used quite satisfactorily. The pressure of the carbon monoxide gas in the reaction should be in the range from normal pressure to 200 kg/cm$^2$ or, preferably, from normal pressure to 100 kg/cm$^2$. The reaction temperature should be in the range from 20° to 150° C. or, preferably, from 40° to 100° C.

The reaction is performed by blowing carbon monoxide gas into the reaction mixture, when the reaction is performed under normal pressure, or by pressurizing the reaction vessel, e.g. autoclave, containing the reaction mixture with carbon monoxide gas, when the reaction is performed under a superatmospheric pressure, and continued usually until no more volume of the carbon monoxide gas can be absorbed by the reaction mixture. The reaction mixture after completion of the reaction contains phenyl pyruvic acid as the desired product in the form of an alkaline earth metal salt, phenyl acetic acid as the principal by-product also in the form of a salt and the cobalt carbonyl catalyst and is processed in the following manner.

Thus, the reaction mixture is first filtered to separate the liquid portion from the solid precipitates mainly of the alkaline earth metal salt of phenyl pyruvic acid formed by the reaction. The liquid portion is then subjected to phase separation into an aqueous solution containing the alkaline earth metal salt of phenyl acetic acid dissolved therein and an organic solution containing the cobalt carbonyl catalyst dissolved therein.

The cake of the precipitates collected by filtration is then dispersed in and acidified with an aqueous solution of an inorganic acid such as a diluted hydrochloric acid so as to isolate the phenyl pyruvic acid which is then extracted from the aqueous mixture with an organic solvent such as diethyl ether and the like. The desired product of phenyl pyruvic acid is obtained by removing the organic solvent from the extract.

The aqueous solution obtained by phase separation of the liquid portion of the reaction mixture is similarly acidified by adding an inorganic acid, e.g. hydrochloric acid, to isolate the free acid which is then extracted from the aqueous solution with an organic solvent, e.g. diethyl ether. Removal of the organic solvent from the extract by evaporation gives phenyl acetic acid as a by-product.

The organic solution obtained by phase separation from the above mentioned aqueous solution can be recycled and reused as such as the catalyst-containing organic feed in the next run of the reaction. As is understood from the above given description, great advantages are obtained by the method of the invention that not only the desired product of phenyl pyruvic acid can be prepared in a high yield but also the by-product of phenyl acetic acid can easily be separated from the cobalt carbonyl catalyst which can be reused as such in the next run by omitting the troublesome and expensive step of catalyst regeneration necessarily undertaken in the prior art method to provide a possibility of economically producing phenyl pyruvic acid in an industrial scale.

Following are the examples and comparative examples to illustrate the inventive method in more detail but not to limit the scope of the invention in any way.

EXAMPLE 1

A reaction mixture was prepared in a stainless steel-made autoclave of 300 ml capacity by introducing 75 ml of methyl isobutyl ketone, 75 ml of water, 18.6% (0.251 mole) of calcium hydroxide, 15.4 g (0.122 mole) of benzyl chloride and 1.2 g (0.0035 mole) of dicobalt octacarbonyl. After flushing the autoclave with carbon monoxide, the reaction mixture under agitation in the autoclave was heated and pressurized with carbon monoxide up to a temperature of 70° C. and a pressure of 50 kg/cm$^2$ to start the reaction which was continued for 6 hours maintaining the above mentioned temperature and pressure. Carbon monoxide could no longer be absorbed by the reaction mixture at the end of the reaction time.

After completion of the reaction, the reaction mixture was discharged out of the autoclave and filtered under pressurization by utilizing the pressure of the carbon monoxide to be separated into a cake of precipitates and the liquid portion which was further subjected to phase separation into an aqueous and an organic solution. The cake of precipitates collected by filtration was transferred into a flask of 500 ml capacity into which 270 ml of a 10% aqueous hydrochloric acid and 150 ml of diethyl ether were added and agitated until the precipitates were completely dissolved. The liquid mixture was subjected to phase separation into the ether solution and the aqueous solution, which latter solution was further treated twice each with 100 ml of diethyl ether in a similar manner. These ether extracts were combined altogether followed by drying over sodium sulfate and then distilled to evaporate the solvent leaving 16.0 g of phenyl pyruvic acid as the desired product. The yield was 80.2% of the theoretical value based on the amount of benzyl chloride.

The aqueous solution obtained by the phase separation of the filtrate from the filtration of the reaction mixture was acidified by adding 70 ml of a 10% aqueous hydrochloric acid and extracted three times each with 100 ml of diethyl ether. The ether extracts were combined altogether followed by drying over sodium sulfate and then distilled to evaporate the solvent leaving 2.3 g of phenyl acetic acid alone. The yield of phenyl acetic acid was 14.1% of the theoretical value based on the amount of benzyl chloride.

The organic solution obtained by the phase separation from the above used aqueous solution contained the cobalt carbonyl catalyst and a small amount of benzyl alcohol dissolved therein.

EXAMPLE 2

The experimental procedure was substantially the same as in Example 1 excepting that methyl isobutyl ketone was replaced with the same volume of acetophenone. The yields of phenyl pyruvic acid and phenyl acetic acid were 72.5% and 12.4%, respectively, of the respective theoretical values based on the amount of benzyl chloride.

EXAMPLE 3

The experimental procedure was substantially the same as in Example 1 except that the reaction was performed under a pressure of 10 kg/cm$^2$ of carbon monoxide instead of 50 kg/cm$^2$. The yields of phenyl pyruvic acid and phenyl acetic acid were 73.5% and 15.0%, respectively, of the respective theoretical values based on the amount of benzyl chloride.

EXAMPLE 4

A reaction mixture was prepared in a glass-made autoclave of 500 ml capacity by introducing 100 ml of methyl isobutyl ketone, 50 ml of water, 9.3 g (0.126 mole) of calcium hydroxide, 7.7 g (0.061 mole) of benzyl chloride and 1.2 g (0.0035 mole) of dicobalt octacarbonyl. After flushing the autoclave with carbon monoxide gas, the reaction mixture under agitation was heated and pressurized with carbon monoxide up to a temperature of 55° C. and a pressure of 2 kg/cm$^2$ to start the reaction which was continued for 10 hours maintaining the above mentioned temperature and pressure. Carbon monoxide could no longer be absorbed by the reaction mixture at the end of the reaction time.

The reaction mixture after completion of the reaction was processed in substantially the same manner as in Example 1 to give yields of 72.1% and 17.9% of the theoretical values for phenyl pyruvic acid and phenyl acetic acid, respectively, based on the amount of benzyl chloride.

EXAMPLE 5

The experimental procedure was substantially the same as in Example 4 except that methyl isobutyl ketone was replaced with the same volume of acetophenone. The yields of phenyl pyruvic acid and phenyl acetic acid were 75.0% and 15.5%, respectively, of the respective theoretical values based on the amount of benzyl chloride.

EXAMPLE 6

The experimental procedure was substantially the same as in Example 4 except that the reaction was performed under normal pressure without pressurization by blowing carbon monoxide gas into the reaction mixture at 50° C. instead of 55° C. and the reaction was continued for 20 hours. The yields of phenyl pyruvic acid and phenyl acetic acid were 71.0% and 22.2%, respectively, of the respective theoretical values based on the amount of benzyl chloride.

EXAMPLE 7

The experimental procedure was substantially the same as in Example 6 except that methyl isobutyl ketone was replaced with the same volume of acetophenone. The yields of phenyl pyruvic acid and phenyl acetic acid were 71.2% and 21.7%, respectively, of the respective theoretical values based on the amount of benzyl chloride.

EXAMPLE 8

Into a stainless steel-made autoclave of 135 ml capacity were introduced 25 ml of water, 6.2 g of calcium hydroxide, 5.1 g of benzyl chloride and 25 ml of the organic solution of methyl isobutyl ketone containing the cobalt carbonyl catalyst and recovered in Example 3 to form a reaction mixture. The reaction and subsequent processing of the reaction mixture were performed in substantially the same manner as in Example 1. The yields of phenyl pyruvic acid and phenyl acetic acid were 73.0% and 15.2%, respectively, of the respective theoretical values based on the amount of benzyl chloride.

EXAMPLE 9

Into a stainless steel-made autoclave of 135 ml capacity were introduced 25 ml of water, 6.2 g of calcium hydroxide, 5.1 g of benzyl chloride and 25 ml of the organic solution of acetophenone containing the cobalt carbonyl catalyst and recovered in Example 2 to form a reaction mixture. The reaction and subsequent processing of the reaction mixture were performed in substantially the same manner as in Example 3. The yields of phenyl pyruvic acid and phenyl acetic acid were 74.2% and 14.0%, respectively, of the respective theoretical values based on the amount of benzyl chloride.

EXAMPLE 10

Into a stainless steel-made autoclave of 135 ml capacity were introduced 25 ml of water, 4.7 g of calcium hydroxide, 3.8 g of benzyl chloride and 50 ml of the organic solution of acetophenone containing the cobalt carbonyl catalyst and recovered in Example 6 to form a reaction mixture. The reaction and subsequent processing of the reaction mixture were performed in substantially the same manner as in Example 6. The yields of phenyl pyruvic acid and phenyl acetic acid were 71.5% and 22.0%, respectively, of the respective theoretical values based on the amount of benzyl chloride.

EXAMPLE 11

Into a stainless steel-made autoclave of 135 ml capacity were introduced 25 ml of water, 4.7 g of calcium hydroxide, 3.8 g of benzyl chloride and 50 ml of the organic solution of acetophenone containing the cobalt carbonyl catalyst and recovered in Example 7 to form a reaction mixture. The reaction and subsequent processing of the reaction mixture were performed in substantially the same manner as in Example 7. The yields of phenyl pyruvic acid and phenyl acetic acid were 72.0% and 21.2%, respectively, of the respective theoretical values based on the amount of benzyl chloride.

What is claimed is:

1. A method for the preparation of phenyl pyruvic acid which comprises:
   (a) adding benzyl chloride, an inorganic basic compound selected from the group consisting of the alkaline earth metal hydroxides, oxides and carbonates and a cobalt carbonyl compound as a catalyst into a liquid reaction medium composed of a binary mixture of water and an organic solvent comprising a liquid ketone compound capable of dissolving the cobalt carbonyl compound and not freely miscible with water at room temperature in such a proportion that the liquid reaction medium is separated into two phases to form a reaction mixture;

(b) bringing the reaction mixture at a temperature of about 20° to about 150° C. into contact with gaseous carbon monoxide under such a pressure that the carbon monoxide is absorbed into the reaction mixture to react with benzyl chloride to form an alkaline earth metal salt of phenyl pyruvic acid (c) separating the precipitates formed in the reaction mixture from the liquid portion, recovering phenyl pyruvic acid from said precipitates by acidification with an inorganic acid and extraction with an organic solvent, separating the remaining reaction mixture into an aqueous phase containing an alkaline earth metal salt of phenyl acetic acid and an organic ketone phase containing said cobalt carbonyl catalyst in re-usable form.

2. The method as claimed in claim 1 wherein the compound of alkaline earth metal is calcium hydroxide.

3. The method as claimed in claim 1 wherein the liquid ketone compound is methyl isobutyl ketone or acetophenone.

4. The method as claimed in claim 1 wherein the cobalt carbonyl compound is dicobalt octacarbonyl.

5. The method as claimed in claim 1 wherein the pressure of carbon monoxide is in the range from normal pressure to 100 kg/cm$^2$.

6. The method as claimed in claim 1 wherein the cobalt carbonyl compound as the catalyst is added to the reaction mixture as a solution in the organic solvent obtained by the phase separation of the liquid portion in the step (c) of a preceding run of the reaction.

7. The method as claimed in claim 1 wherein the amount of benzyl chloride is in the range from 1 to 50% by weight based on the amount of the organic solvent.

8. The method as claimed in claim 1 wherein the amount of water is in the range from 10 to 200% by weight based on the amount of the organic solvent.

9. The method as claimed in claim 1 wherein the amount of the inorganic basic compound is in the range from 1.1 to 2.5 moles per mole of the benzyl chloride.

10. The method as claimed in claim 1 wherein the amount of the cobalt carbonyl compound is in the range from 0.01 to 1 mole per mole of the benzyl chloride.

11. The method as claimed in claim 1, wherein said liquid ketone organic solvent is selected from the group consisting of methyl isobutyl ketone, acetophenone, diisopropyl ketone, methyl isopropyl ketone, dibutyl ketone and cyclopentanone.

12. The method as claimed in claim 1, wherein said temperature is about 40° to about 100° C.

* * * * *